United States Patent [19]

Aoki et al.

[11] Patent Number: 5,035,711
[45] Date of Patent: Jul. 30, 1991

[54] TRANSCUTANEOUSLY IMPLANTABLE ELEMENT

[75] Inventors: Hideki Aoki, Ibaraki; Masaru Akao, Kawasaki; Yoshiharu Shin, Higashimurayama, all of Japan

[73] Assignee: Kabushiki Kaisya Advance Kaihatsu Kenkyujo, Tokyo, Japan

[21] Appl. No.: 577,820

[22] Filed: Sep. 5, 1990

Related U.S. Application Data

[63] Continuation of Ser. No. 470,414, Jan. 29, 1990, abandoned, which is a continuation of Ser. No. 387,388, Jul. 31, 1989, abandoned, which is a continuation of Ser. No. 267,613, Nov. 2, 1988, abandoned, which is a continuation of Ser. No. 110,539, Oct. 17, 1987, abandoned, which is a continuation of Ser. No. 917,247, Oct. 7, 1986, abandoned, which is a continuation of Ser. No. 592,436, Mar. 22, 1984, abandoned.

[30] Foreign Application Priority Data

| Mar. 24, 1983 | [JP] | Japan | 58-47896 |
| Sep. 6, 1983 | [JP] | Japan | 58-162645 |
| Sep. 12, 1983 | [JP] | Japan | 58-166502 |
| Oct. 28, 1983 | [JP] | Japan | 58-200733 |

[51] Int. Cl.$^5$ .............................................. A61F 2/02
[52] U.S. Cl. ..................................... 623/11; 623/66
[58] Field of Search ............................ 623/11, 12, 66

[56] References Cited

U.S. PATENT DOCUMENTS

| 3,663,965 | 5/1972 | Lee, Jr. et al. | |
| 3,783,868 | 1/1974 | Bokros | 3/1 X |
| 3,918,100 | 11/1975 | Shaw et al. | 623/16 |
| 3,919,723 | 11/1975 | Heimke et al. | 3/1.9 |
| 3,952,334 | 4/1976 | Bokros et al. | 3/1 |
| 4,183,357 | 1/1980 | Bentley et al. | 623/66 X |
| 4,437,191 | 3/1984 | vander Zel et al. | 623/16 X |

FOREIGN PATENT DOCUMENTS

| 515164 | 2/1981 | Australia . | |
| 518908 | 10/1981 | Australia . | |
| 0039188 | 4/1981 | European Pat. Off. . | |
| 2910627 | 9/1980 | Fed. Rep. of Germany | 3/1.91 |
| 1554943 | 10/1979 | United Kingdom . | |

OTHER PUBLICATIONS

Shin, Y. et al., "Tissue Responses to Hydroxyapatite, $\beta$-Tricalcium Phosphate and Glassy Carbon Percutaneously Implanted in Dogs", The 15th Annual Meeting of the Society for Biomaterials (1989).

Shin, Y. et al., "Skin Tissue Reactions to Hydroxylapatite, $\beta$-tricalciumphosphate and Glassy Carbon", vol. 1, Ionic Polymers, Ordered Polymers for High Performance Materials, Biomaterials (1988).

Shin, Y. et al., "Sintered Hydroxylapatite for a Percutaneous Device", Bioceramics (1989).

Trans, Am. Soc. Artif. Inter. Organs, vol. XXIV, pp. 484–489 (1978).

Diabetes, vol. 30, Dec. 1981, pp. 1072–1075.

Horm. Metab. Res., 487:339–342 (1974).

Diabetes Care, vol. 5, No. 3, May–Jun. 1982, pp. 218–221.

Diabetes, vol. 23, No. 9, pp. 732–738 (Sep. 1974).

Jarcho, M., Clin. Orthop. Relat. Res. 157,259 (1981).

Rabalais, M. et al., J. Periodontol. 52, 11, 680 (1981).

Osborn, J. F. et al., Biomaterials 1 2, 108 (1980).

Froum, S. J. et al., J. Periodontol, 53 12, 719 (1982).

*Primary Examiner*—Alan Cannon
*Attorney, Agent, or Firm*—Finnegan, Henderson, Farabow, Garrett & Dunner

[57] ABSTRACT

A transcutaneously implantable element in which at least a portion thereof in contact with the cutaneous tissue of a living body is composed of a ceramic material comprising, as the main raw material, at least one member selected from the group consisting of hydroxyapatite, tricalcium phosphate, and tetracalcium phosphate, and which comprises (a) an electrically conductive member for electrically connecting the interior and exterior of the living body to each other or (b) a through hole for mechanically connecting the interior and exterior of the living body to each other.

This transcutaneously element can be semipermanently and safely used in a living body without causing any undesirable bacterial infection, bleeding, and background noise.

3 Claims, 4 Drawing Sheets

TRANSCUTANEOUSLY IMPLANTABLE ELEMENT

This application is a continuation, of application Ser. No. 07/470,414, filed Jan. 29, 1990, now abandoned, which is a continuation of U.S. Ser. No. 07/387,388, filed July 31, 1989, now abandoned, which is a continuation of U.S. Ser. No. 07/267,613, filed Nov. 2, 1988, now abandoned, which is a continuation of U.S. Ser. No. 07/110,539 filed Oct. 27, 1987, now abandoned, which is a continuation of U.S. Ser. No. 06/917,247, filed Oct. 7, 1986, now abandoned, which is a continuation of U.S. Ser. No. 06/592, 436, filed Mar. 22, 1984, now abandoned.

BACKGROUND OF THE INVENTION

1. Field of the Invention

The present invention relates to a transcutaneously implantable element in which at least a portion thereof in contact with a cutaneous tissue is composed of a ceramic material comprising, as the main raw material, at least one member selected from the group consisting of hydroxyapatite, tricalcium phosphate, and tetracalcium phosphate.

2. Description of the Prior Art

Transcutaneously implantable elements such as a percutaneous electrode connecter or a cannula are used as an electrical terminal for collecting biological information such as blood pressure, flow rate of blood, temperature, and electrocardiosignals, or as a port for taking and injecting blood through the through hole thereof, for example, as a port for effecting transfusion, injection of liquid medicines, or artificial kidney dialysis. When these transcutaneously implantable elements are used, one end of the element is placed on the skin of a living body and the other end thereof is buried under the skin. Conventional transcutaneously implantable elements already proposed are mainly composed of a so-called bioinactive material, for example, a silicone rubber or a fluorine-contained resin.

However, strictly speaking, these transcutaneously implantable elements are only extraneous substances to a living body, and a portion of the living body in which the element is mounted is in a traumatized state. Therefore, bacterial infection may be caused from the interstice between that portion and the element. Accordingly, these transcutaneously implantable elements cannot possibly withstand a long period of service. Furthermore, the transcutaneously implantable elements involve problems in that since they cannot be firmly implanted in the living body, bleeding may occur due to, for example, shaking, and since noise such as a so-called artefact cannot be eliminated when bioelectrical signals, for example, electrocardiosignals, are collected, bioinformation cannot be stably gathered. Therefore, the transcutaneously implantable elements have not been widely accepted.

For example, with a so-called drug delivery system for an artificial pancreas or the like (see Kraus Heylman, "Therapeutic Systems" published by Georg Thieme Publishers, 1978) recently developed rapidly, the problems of the injection route and the infinitesimal quantity quantitative injection of drugs such as insulin have not been solved as yet (Medical Instrument Society Journal, Vol. 53, No. 2, 1973, infra p. 90). Therefore, there is now an increasing demand for a transcutaneously implantable element which can be semi-permanently and safely used as an injection inlet for drugs.

On the other hand, as the excellent bio-compatibility and bone-deriving ability of sintered bodies of hydroxyapatite, tricalcium phosphate or the like have been clarified recently, the utilization of these sinters as an artificial dental root or an artificial bone has been proposed and practically effected. However, the physiological reactivity of the sinters to the cutaneous tissue of a living body has not been solved in the prior art.

SUMMARY OF THE INVENTION

Accordingly, the object of the present invention is to eliminate the above-mentioned problems in the prior art and to provide a transcutaneously implantable element capable of being semi-permanently and safely used without causing any undesirable bacterial and infection, bleeding, and background noise.

Other objects and advantages of the present invention will be apparent from the description set forth hereinbelow.

In accordance with the present invention, there is provided a transcutaneously implantable element in which at least a portion thereof in contact with the cutaneous tissue of a living body is composed of a ceramic material comprising, as the main raw material, at least one member selected from the group consisting of hydroxyapatite, tricalcium phosphate, and tetracalcium phosphate, and which comprises (a) an electrically conductive member for electrically connecting the interior and exterior of the living body to each other or (b) a through hole for mechanically connecting the interior and exterior of the living body to each other.

DESCRIPTION OF THE PREFERRED EMBODIMENTS

The present invention will now be better understood from the following descriptions presented in connection with the accompanying drawings in which.

The material composition, method of preparation, shape, structure, and embodiment of use of the transcutaneously implantable element, plug·or conduit of the present invention will be described in detail.

Material Composition and Preparation

The term "ceramic material" as used herein means a sinter comprising, as the main raw material, at least one member selected from the group consisting of hydroxyapatite, tricalcium phosphate, and tetracalcium phosphate, and a coated material comprising a substrate, for example, a metal or a ceramic, flame sprayed- or sinter-coated with the above-mentioned sinter The ceramic material may contain various additives such as $MgO$, $Na_2O$, $K_2O$, $CaF_2$, $Al_2O_3$, $SiO_2$, $CaO$, $Fe_2O_3$, $MnO$, $MnO_2$, $ZnO$, $C$, $SrO$, $PbO$, $BaO$, $TiO_2$, and $ZrO_2$ in order to enhance the sinterability, strength, and porosity thereof, and other properties.

The term "hydroxyapatite" as used herein includes a pure hydroxyapatite whose chemical composition is represented by the formula $Ca_{10}(PO_4)_6(OH)_2$ and a modified hydroxyapatite containing 1% to 10% of a carbonate ($CO_3$) ion, a fluoride ion or a chloride ion in place of a hydroxyl (OH) ion in the formula $Ca_{10}(PO_4)_6(OH)_2$. The hydroxyapatite may contain well-known additives such as $Ca_3(PO_4)_2$, $MgO$, $Na_2O$, $K_2O$, $CaF_2$, $Al_2O_3$, $SiO_2$, $CaO$, $Fe_2O_3$, $MnO$, $MnO_2$, $ZnO$, $C$, $SrO$, $PbO$, $BaO$, $TiO_2$, and $ZrO_2$ in order to enhance the sinterability, strength, and porosity thereof, and other properties.

Where the hydroxyapatite is used as a composite material with a polymeric material, the polymeric material may be selected from resins having a relatively low toxicity, for example, polyethylene, polypropylene, polymethyl methacrylate, polyurethanes, polyesters, ABS resins, fluorine-contained resins, polycarbonates, polysulfone, epoxy resins, silicones, diallyl phthalate resins, and furan resins.

On the other hand, the methods of preparation of the ceramic material include a so-called sintering method in which the raw material is sintered singly or on a substrate such as a metal, plastics or ceramics and vapor deposition methods such as a plasma spray coating method, an ion beam deposition method and a vacuum evaporation method in which the raw material is plasma sprayed on a substrate such as a metal or ceramics.

For example, the single sintered material is generally obtained by compress molding a raw material comprising hydroxyapatite, tricalcium phosphate or tetracalcium phosphate in a mold or a rubber press under a pressure of approximately 500 to 3,000 kg/cm$^2$, to obtain a compact having a desired shape, and then subjecting the compact to a sintering treatment at a temperature of approximately 700° C. to 1,300° C. For further details of other methods of preparation and the material composition, reference will be made to the following publications: Japanese Unexamined Patent Publication (Kokai) Nos. 51-40400, 52-64199, 52-82893, 52-142707, 52-147606, 52-149895, 53-28997, 53-75209, 53-111000, 53-118411, 53-144194, 53-110999, 54-94512, 54-158099, 55-42240, 55-51751, 55-56062, 55-130854, 55-140756, 56-18864, 56-45814, 56-143156, and 56-166843, and Japanese Examined Patent Publication (Kokoku) Nos. 57-40776, 57-40803, and 58-39533.

From the standpoint of joining with the cutaneous tissue of a living body, an especially useful sinter for the present invention has a relative density (based on the density of a single crystal of hydroxyapatite) of 60% to 99.5%, desirably approximately 85% to 95%. Where the transcutaneously implantable element of the present invention is used as an injection route of a liquid medicine in the drug delivery system, as described hereinafter, a portion of the element in contact with the cutaneous tissue may be provided with a porous member.

The porous members usable for this purpose are those which are able to function as a barrier layer against the penetration of the tissue of a living body into the passage of liquid medicines and the spontaneous diffusion of the concentration of drugs. Examples of such porous members are porous resin films such as a porous Teflon film; sintered porous resins which are used as a filter medium or a filter membrane; porous ceramics such as sintered porous alumina; porous glass; sintered porous metals such as sintered platinum; electrochemical diaphrams, such as porcelain diaphram, as used in the electrolytic industry; dialysis membranes; and porous materials consisting of calcium phosphate which are disclosed in the above-mentioned patent publications. These porous members may be in the form of a film, sheet, cylinder or the like, having an appropriate average pore diameter, and may be suitably selected depending on the intended use.

To ensure that it effectively functions as the barrier layer, it is desirable that the porous member usually have an average pore diameter of $0.01\mu$ to 1 mm, preferably $0.5\mu$ to $700\mu$. Generally, the average pore diameter of the porous member is variable depending on the site to be implanted, the implantation depth, the molecular weight and concentration of the drug used, and the form of energy used for the drug injection.

Especially when ultrafiltration membranes for artificial dialysis such as those made of polymeric materials having a fraction molecular weight of approximately 10,000 to 50,000, for example, regenerated cellulose, polyacrylonitrile, polymethyl methacrylate, cellulose acetate, polycarbonate, polysulfone, and polyamide, or filter or precision filter membranes having an average pore diameter of approximately $0.5\mu$ to $100\mu$, are used as the porous member of the present invention, these membranes function fairly satisfactorily as the barrier layer. However, because of their high filtration resistance, it is not always preferable to use mechanical energies such as pressure as the injection energy for drugs. In this case, the use of electrochemical driving forces such as iontophoresis or electroendosmosis, as described hereinafter, is preferable. For example, as is well known, electroendosmosis is a phenomenon wherein when an electrical voltage is applied to a porous body having pores, a liquid is quantitatively migrated to either of a cathode and an anode due to the electrochemical properties at the interface. The transcutaneously implantable element of the present invention is also, applicable to this type of method. In this case, selection of a liquid medicine and a porous member is carried out after taking into account their interfacial electrochemical properties.

Shape and Structure

The shape of the transcutaneously implantable element of the present invention is variable, depending on the end use thereof. A typical example of the element is described below in detail with reference to the accompanying drawings.

Figure 1:
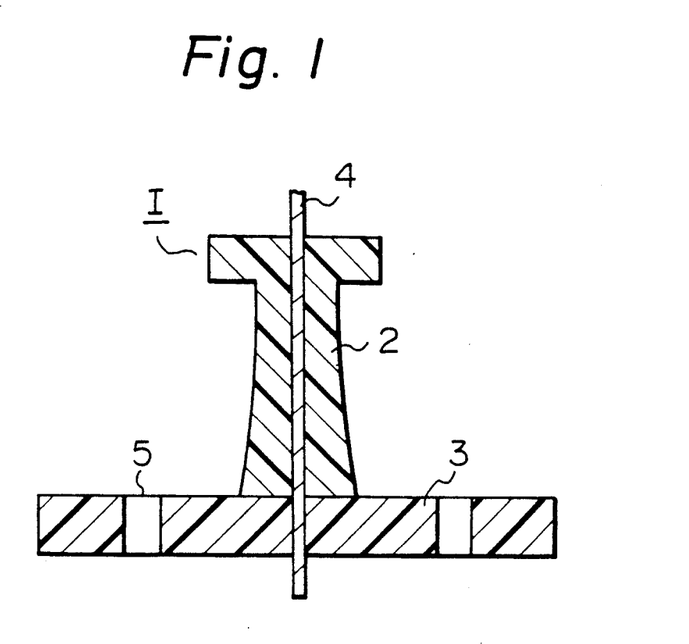
FIGS. 1 to 8 are schematic cross sectional views of the transcutaneously implantable elements I, II, III, IV, V, VI, VII, and VIII according to the present invention.

FIG. 1 is a cross sectional view showing an example of the transcutaneously implantable element of the present invention. In the drawing, a transcutaneously implantable element I used as an electrical terminal comprises an element head 2 and an element bottom 3 integrally combined with each other. Both the head 2 and the bottom 3 are composed of the ceramic material of the present invention. Within the element 1, there is buried an electrically conductive member 4 such as gold wire, silver wire, platinum wire, alloy wire, and carbon fiber to electrically connect the interior of a living body to the exterior thereof. If necessary, one or not less than two holes 5 for suturing are bored in the bottom 3.

The transcutaneously implantable element 1 having the above-mentioned structure is implanted in such a manner that the bottom 3 is fixedly buried under the skin and the upper end of the head 2 is protruded above the skin. After this implanting, the element I is used as an electrical terminal for gathering bioelectrical signals or the like, or for connecting bioelectrically stimulating devices such as a pacemaker.

Figure 2:
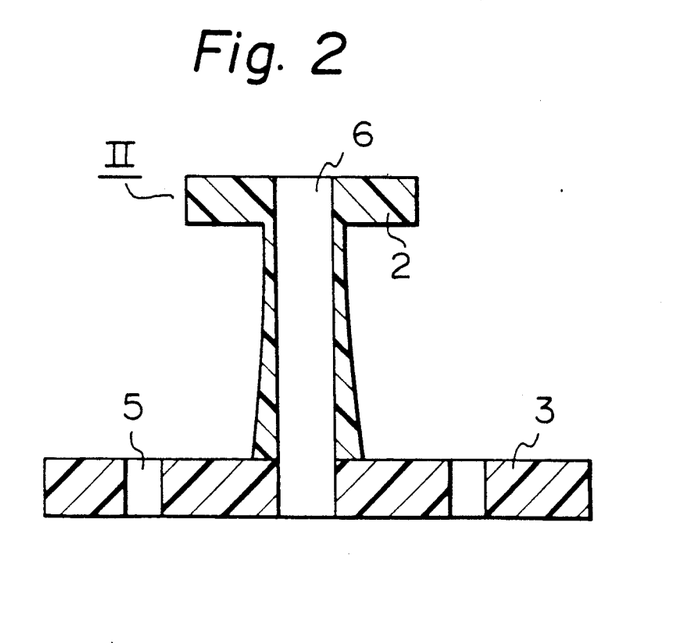

Similarly, FIG. 2 is a cross sectional view showing an example of the transcutaneously implantable element of the present invention which is used as a bioplug. The transcutaneously implantable element II has the same structure as the transcutaneously implantable element I except that, in place of the conductive member 4, a through hole 6 is provided for connecting the interior of a living body to the exterior thereof. In the drawing, the same reference numerals denote the same parts as shown in FIG. 1.

In the other hand, since a desired object can be attained so long as a portion of the transcutaneously implantable element in contact with the cutaneous tissue is composed of the ceramic material of the present invention, the transcutaneously implantable element may be of a structure wherein only an essential portion thereof is composed of the sinter and the other portions are composed of other materials such as synthetic resins. Alternatively, the essential portion may be composed of a coated material consisting of a ceramic material comprising, as the main raw material, at least one member selected from the group consisting of hydroxyapatite, tricalcium phosphate, and tetracalcium phosphate, (for examples, see, Japanese Unexamined Patent Publication (Kokai) Nos. 52-82893, 53-28997, 53-75209, 53-118411, and 58-39533).

For example, a metallic microneedle coated with a flame sprayed or sintered layer of hydroxyapatite at the peripheral surface thereof can be used as the electrically transcutaneously implantable element.

Figure 3:
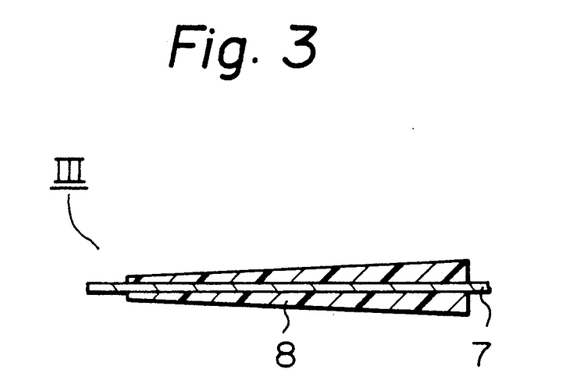

FIG. 3 is a cross sectional view of a transcutaneously implantable element III in the form of microneedle. The element III comprises a metallic needle 7, such as a gold needle, coated with a coated or flame sprayed layer 8 consisting of the ceramic material of the present invention. When this type of element is used, it is implanted merely by piercing the skin of a patient. Furthermore, the transcutaneously implantable element of the present invention may be used as an inlet for dosing drugs in drug delivery systems, as described hereinafter. In this case, transcutaneously implantable elements having the shapes shown in FIGS. 4 through 8 are especially useful.

Figure 4:
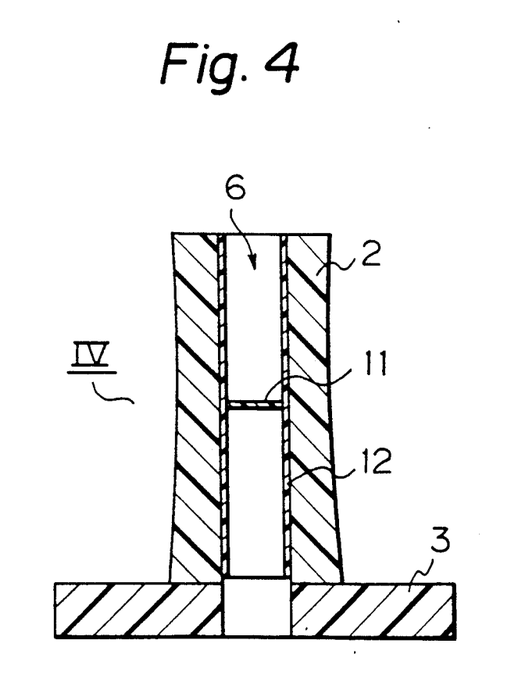

FIG. 4 is a cross sectional view showing another example of the transcutaneously implantable element of the present invention. In the drawing, a transcutaneously implantable element IV used as an inlet for injecting drugs comprises an element head 2 and an element bottom 3 integrally combined with each other. Both the head 2 and the bottom 3 are composed of the ceramic material of the present invention. Within the head 2, there is provided a cylinder 12 which is made of a metal or a synthetic resin such as a silicone resin and is equipped with a membrane filter for removing bacteria, such as a *Millipore Filter* ®, at the middle or end portion thereof. A desired drug is injected into a living body through a through hole 6.

Figure 5:
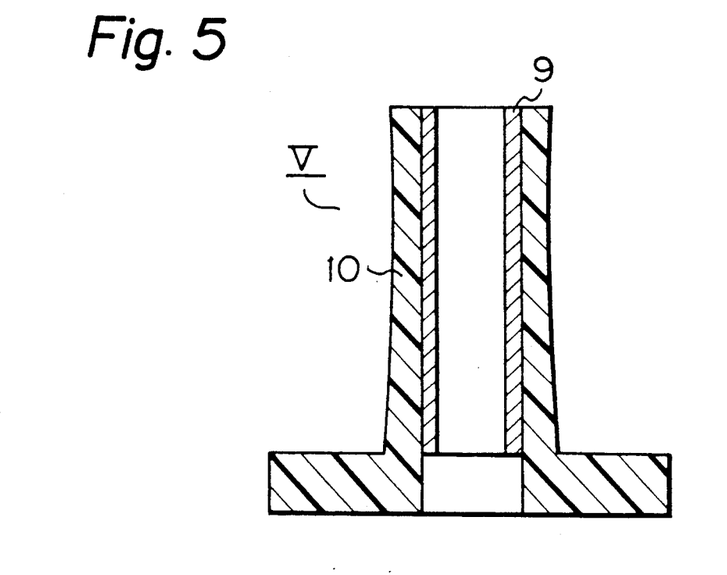

FIG. 5 is a cross sectional view of a transcutaneously implantable element V in the form of a microtube. The element V comprises a metallic tube 9, such as a gold tube, coated with a coating layer 10 consisting of the ceramic material of the present invention at the peripheral surface thereof. This element is implanted merely by being buried in the skin of a patient.

Figure 6:
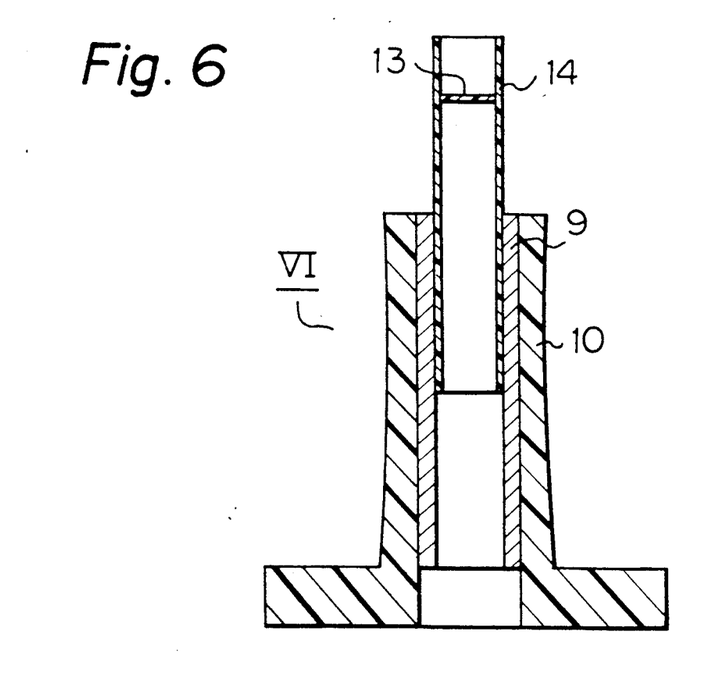

FIG. 6 is a cross sectional view of a transcutaneously implantable element VI in the form of a microtube. The element VI comprises a metallic tube 9, such as a gold tube, coated with a sinter coating or flame-sprayed layer 10 consisting of hydroxyapatite at the peripheral surface thereof and a filter means 14 for removing bacteria having a filter 13 connected to the end of the head. This element is implanted merely by being buried in the skin of a patient.

Figure 7:
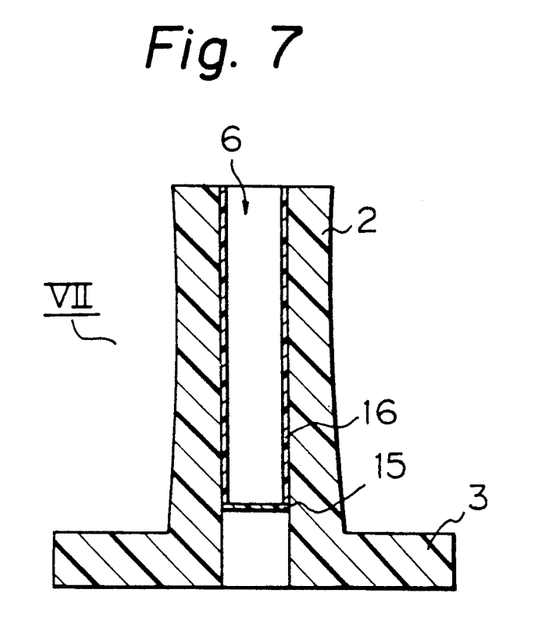

Furthermore, to hinder the spontaneous diffusion of drugs as much as possible, it is possible to provide a portion of the transcutaneously implantable element in contact with the tissue of a living body with a barrier layer, as shown in FIG. 7. In the drawing, a transcutaneously implantable element VII used as an inlet for injecting drugs comprises an element head 2 and an element bottom 3 integrally combined with each other, both the head 2 and the bottom 3 being composed of the ceramic material of the present invention, and a cylinder 16 made of a metal on a synthetic resin such as a silicone resin and provided in the head 2 and which is provided, at the middle or end portion thereof, with a porous member 15 such as an ultrafiltration member, for example, Amicon PM-30, 0.22$\mu$ millipore membrane filter or a sintered polyethylene filter having an average pore diameter of 15$\mu$. A desired drug is injected into a living body through a through hole 6 of the cylinder 16.

Figure 8:
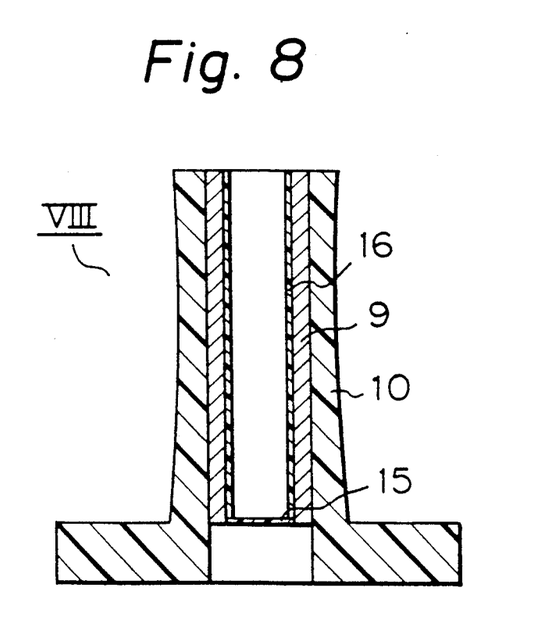

FIG. 8 is a cross sectional view of a transcutaneously implantable element VIII in the form of a microtube. The element VIII comprises a metallic tube 9, such as a gold tube, coated with a coating or flame-sprayed layer 10 consisting of the ceramic material of the present invention, and a porous member 15 consisting of a sintered alumina having an average pore size of 3$\mu$ provided in the lower end of the tube 9.

A plastic drug reservoir may be integrally joined with the top of the transcutaneously implantable elements having the shapes shown in FIGS. 4 through 8 to provide a drug delivery system.

As is apparent from the foregoing, the transcutaneously implantable element of the present invention can assume a variety of shapes, structures and sizes, and thus, are not limited to any specific form.

It is evident from the above-mentioned description that the transcutaneously implantable element of the present invention composed of the ceramic material comprising, as the main raw material, at least one member selected from the group consisting of hydroxyapatite, tricalcium phosphate, and tetracalcium phosphate, has an adaptability to a living body and, further, it forms an interface junction with the cutaneous tissue, such as epidermis and dermis, of the living body to be stably implanted in the living body. Therefore, the transcutaneously implantable element of the present invention can be widely used as a terminal for connecting an external electric source to a heart pacemaker, an outlet for blood dialysis, and a terminal for connecting a biowire having sensor elements, for example, an ultrasonic sensor element, at the tip thereof to an external measuring instrument. Accordingly, the transcutaneously implantable element of the present invention is very useful in the fields of diagnosis, therapy, animal experiments, and the like.

Furthermore, the transcutaneously implantable element having a through hole has wide application as an inlet for dosing drug in drug delivery systems. When this element is used as the drug inlet, it is buried and implanted in the skin of a living body and a tube for feeding a liquid medicine which is quantitatively driven by means of a micropump or the like can be connected only to the implanted element.

Now, as an especially useful embodiment of the transcutaneously implantable element of the present invention, there is mentioned its use as an injection inlet for a so-called iontophoresis in which the dosing of a drug is electrochemically driven.

For example, the injection of insulin.HCl into an artificial pancreas has been conventionally effected by using a microquantitative injection pump. By merely connecting the transcutaneously implantable element to the positive pole of a direct current source instead of using the pump, it is possible to introduce insulin.cation into a living body very easily and stably.

A conventional iontophoresis is applied from the upper surface of the skin. In this case, the cutaneous keratin layer acts exclusively as an electrical and physical barrier which renders the introduction of a relatively large molecule, e.g., insulin, difficult. Contrary to this, in accordance with the transcutaneously implantable element of the present invention, since the cutaneous keratin layer can no longer function as the barrier, a remarkable reduction in the impedance and physical resistance results. Furthermore, quantitative injection or feedback injection by a glucose sensor can be readily attained by controlling the current value (in the case of insulin, usually within the range of several $\mu A$ to several mA when direct current or pulse direct current is used). That is, where the transcutaneously implantable element is used in iontophoresis, instead of using a liquid medicine impregnation technique (generally a water retainable material is used such as a sponge or cotton, or a hydrophilic gel) for conventional iontophoresis, a conduit for injecting a liquid medicine is connected to the element to provide a passage for the medicine. A non-barrier member consisting of well-known bioelectrodes (for example, Japanese Unexamined Patent Publication No. 58-10066 or Japanese Patent Application No. 56-106935) is attached on another site of the skin. A direct current is then passed between the working electrode and the counter electrode (if an ionic drug is a cation, the working electrode is an anode).

For further details of the iontophoresis itself, refer to the above-mentioned patent publications.

EXAMPLES

The present invention will be illustrated by, but is by no means limited to, the following examples.

EXAMPLE I

1. Preparation of a transcutaneously implantable element 0.5 mole/l of calcium hydroxide and 0.3 mole/l of a phosphorous acid solution were gradually mixed dropwise to react these materials at a temperature of 37° C. for one day. The resultant reaction mixture was filtered and dried to obtain hydroxyapatite powder. 3 g of the synthetic powder was filled in a mold having an inner diameter of 15 mm and molded together with a fine gold wire having a diameter of 0.05 mm, under a pressure of 800 kg/cm², to obtain a compact having a bulk density of 1.6 g/cm³. This compact was cut and processed by using a lathe and a dental diamond bar to provide an element head (FIG. 1).

Similarly, 4.5 g of the above-synthesized powder was filled in a mold having an inner diameter of 30 mm together with a gold wire, to obtain a compact specimen, after which molding, cutting, and processing were effected to obtain an element bottom (FIG. 1). The gold wires of these compact specimens were then joined together, and a gelatinous apatite powder which was thoroughly kneaded with water in a mortar was applied to the junction of the compacts to bond them to each other. The resultant composite product was subjected to a sintering treatment at a temperature of 1,250° C. for 1 hour, to obtain a transcutaneously implantable element, as shown in FIG. 1, having a compressive strength of 5,000 kg/cm², a bending strength of 1,200 kg/cm², a relative density of 95%.

In the resultant transcutaneously implantable element, the element bottom had a diameter of 24 mm and a thickness of 3 mm, and the neck of the element head had an average diameter of 6 mm.

Further, when the sintering temperature was 1,100° C., the resultant sinter had a relative density of 85%, a compressive strength of 3,000 kg/cm², and a bending strength of 700 kg/cm².

2. Animal experiment

The above-mentioned transcutaneously implantable element was buried in the side abdominal skin of a crossbred adult dog and variations in the buried site over a period of time were observed. About two weeks after the operation, it was found that the element was tightly combined and joined with the skin tissue at the bottom and neck portions thereof to an extent wherein it could not be forcibly separated from the skin tissue. Even after the lapse of one year, no abnormal phenomenon such as inflammation reaction could be observed with the naked eye.

A conventional histological examination also revealed the absence of any inflammatory cells.

On the other hand, when a transcutaneously implantable element of the same shape made of a silicone rubber was buried as a control, even four weeks after the operation, joining of the element with the skin tissue could not be observed and inflammatory rubefaction had already appeared. Two months after the operation, the inflammation had worsened and had began to suppurate, and three months after the operation, the element became detached from the skin.

EXAMPLE II

A sinter in the form of a small column with a diameter of 3 mm, containing a gold wire 0.05 mm in diameter, was prepared in a manner similar to that described in Example I, except that a powdery mixture of the above-mentioned hydroxyapatite powder and, as additives, 7% of $Ca_3(PO_4)_2$, 0.8% of $MgO$, 1.8% of $Na_2O$, 0.2% of $K_2O$, and 0.2% of $CaF_2$ were used as the starting material. The resultant sinter was subjected to an abrasion treatment using an abrasive to obtain a microneedle-like element having the shape shown in FIG. 3.

The sinter portion of the element had a length of 10 mm and a maximum diameter of 1 mm.

Then, a predetermined number of the microneedle-like elements were pierced and buried in the thorax of an adult dog, in such a manner that their tips were located under the skin. Approximately three weeks after the elements were buried, the elements were completely joined with the cutaneous tissue and implanted therein.

The gold wire of the element was then connected to an electrocardiograph to effect measurement. As a result, a very clear electrocardiogram from which any influence due to cutaneous impedance or artefact was completely eliminated was obtained.

EXAMPLE III

1. Preparation of a transcutaneously implantable element

Synthetic powder of tricalcium phosphate was filled in a mold and was molded together with a fine gold wire having a diameter of 0.05 mm under a pressure of 800 kg/cm$^2$ to obtain a compact having a bulk density of 1.6 g/cm$^3$. The resultant compact was cut and processed by using a lathe and a dental diamond bar to provide an element head (FIG. 1). Similarly, the above-mentioned synthetic powder was filled in a mold together with a gold wire, to obtain a compact, after which compression molding, cutting, and processing were effected to obtain an element bottom (FIG. 1). The gold wires of these compacts were then joined together, and a gelatinous apatite powder which was thoroughly kneaded with water in a mortar was applied to the junction of the compacts to bond them to each other. The resultant composite product was subjected to a sintering treatment at a temperature of 1,200° C. for 1 hour to obtain a transcutaneously implantable element, as shown in FIG. 1, having a compression strength of 4,300 kg/cm$^2$, a bending strength of 1,000 kg/cm$^2$, and a relative density of 93%.

In the resultant transcutaneously implantable element, the element bottom had a diameter of 20 mm and a thickness of 2 mm and the neck of the element head had a diameter of 5 mm.

2. Animal experiment

The above-mentioned transcutaneously implantable element was buried in the side abdominal skin of a crossbred adult dog and variations in the buried site over a period of time were observed. About two weeks after the operation, it was found that the element was tightly combined and joined with the skin tissue at the bottom and neck portions thereof, to an extent that it could not be forcibly separated from the skin tissue. Even after the lapse of one year, no abnormal phenomenon such as inflammation reaction could be observed with the naked eye.

A conventional histological examination also revealed the absence of any inflammatory cells.

On the other hand, when a transcutaneously implantable element of the same shape made of a silicone rubber was buried as a control, even four weeks after the operation, no joining of the element with the skin tissue could be observed and inflammatory rubefaction had already appeared. Two months after the operation, the inflammable had worsened and began to suppurate, and three months after the operation, the element became detached from the skin.

EXAMPLE IV

A sinter in the form of a small column with a diameter of 3 mm, containing a gold tube having a diameter of 1 mm, was prepared in a manner similar to that described in Example III, except that a powdery mixture of the above-mentioned tricalcium phosphate powder and, as additives, 0.8% of MgO, 1.8% of Na$_2$O, 0.2% of K$_2$O, and 0.2% of CaF$_2$ were used as the starting material. The resultant sinter was subjected to an abrasion treatment using an abrasive to obtain an element in the form of a microtube having the shape shown in FIG. 5.

The sinter portion of the element had a length of 8 mm and an outer diameter of 2 mm.

The element was then pierced and buried in the thorax of an adult dog so that the bottom thereof was located under the skin. Approximately three weeks after the element was buried, the element was completely joined with the cutaneous tissue and implanted therein.

Next, the end of the element head was connected to a conduit filled with physiological saline to measure the DC resistance (an electrode for an electrocardiogram, Lectroad ®, manufactured by Advance Electrode Co., Ltd. was attached to another portion of the shaved thorax as the counter electrode). As a result, a resistance value of 3.6 kΩ was obtained, confirming a remarkable reduction in the resistance when compared to the usual cutaneous resistance through the keratin layer of approximately 100 kΩ.

EXAMPLE V

70% by weight of tricalcium phosphate and 30% by weight of tetracalcium phosphate were mixed. The resultant mixture was molded into an element head and an element bottom, and the head and bottom were joined together in a manner similar to that described in Example 1. The resultant composite product was subjected to a sintering treatment at a temperature of 1,250° C. for 1 hour to obtain a transcutaneously implantable element as shown in FIG. 2.

The same animal experiment as in Example 1 was carried out using the resultant above transcutaneously implantable element. Almost the same results as those obtained in Example IV were obtained.

EXAMPLE VI

A coating layer of tricalcium phosphate was formed on the surface of a core consisting of a fine gold wire of 0.05 mm inner diameter by using a plasma spray coating method. The coated core was sintered at a temperature of 1,200° C. for 10 minutes, and the resultant sinter was abrasion-treated with an abrasive to obtain a transcutaneously implantable element in the form of a microneedle as shown in FIG. 3.

The same animal experiment as in Example II was then carried out using the resultant above element. Substantially the same results were obtained as in Example II.

Example VII

A coating layer of tetracalcium phosphate was formed on the surface of a core consisting of a fine gold wire of 0.05 mm inner diameter by using, as the starting material, a powdery mixture of tetracalcium phosphate powder and, as additives, 7% of Ca$_3$(PO$_4$)$_2$, 0.8% of MgO, 1.8% of Na$_2$O, 0.2% of K$_2$O, and 0.2% of CaF$_2$, in the same manner as that of Example VI. After the coated core was sintered, it was abrasion-treated with an abrasive to obtain a microneedle-like element having the shape shown in FIG. 3.

When the same animal experiment as in Example VI was carried out, using the resultant above element, substantially the same results were obtained as in Example VI.

EXAMPLE VIII

1. Preparation of a transcutaneously implantable element

Synthetic hydroxyapatite powder obtained in the same manner as in Example I was filled in a mold and compression molded under a pressure of 800 kg/cm$^2$, to obtain a compact having a through hole 2 mm in diameter and having a bulk density of 1.6 g/cm$^3$. The compact specimen was cut and processed by using a lathe and a dental diamond bar to obtain an element head (FIG. 1). Similarly, the above-mentioned synthetic powder was filled in a mold and was molded, to obtain a compact, after which cutting and processing were carried out to obtain an element bottom (FIG. 1). The through holes of these compacts were joined together and a gelatinous apatite powder which was thoroughly kneaded with water in a mortar was applied to the junctions of the compacts to bond them to each other. The resultant composite product was subjected to a sintering treatment at a temperature of 1,250° C. for 1 hour to obtain a transcutaneously implantable element, as shown in FIG. 4, having a compressive strength of 5,000 kg/cm$^2$, a bending strength of 1,200 kg/cm$^2$, and a relative density of 95%.

In the resultant transcutaneously implantable element, the element bottom had a diameter of 5.4 mm and a thickness of 2 mm, and the neck of the element head had an outer diameter of 4 mm and an inner diameter of 2 mm.

Furthermore, when the sintering temperature was 1,100° C., the resultant sinter had a relative density of 85%, a compressive strength of 3,000 kg/cm$^2$, and a bending strength of 700 kg/cm. Finally, a synthetic resin cylinder equipped with a filter means for removing bacteria was provided in the element, as shown in FIG. 4, to provide a sample.

2. Animal experiment

The above-mentioned transcutaneously implantable element was buried in the side abdominal skin of a crossbred adult dog and variations in the buried site over a period of time were observed. About two weeks after the operation, it was found that the element was tightly combined and joined with the skin tissue at the bottom and neck portions thereof, to an extent that it could not be forcibly separated from the skin tissue. Even after the lapse of one year, no abnormal phenomenon such as inflamation reaction could be observed with the naked eye.

A conventional histological examination also revealed the absence of any inflamed cells.

On the other hand, when a transcutaneously implantable element of the same shape made of a silicone rubber was buried as a control, even four weeks after the operation, no joining of the element with the skin tissue could be observed and inflammatory rubefaction had already appeared. Two months after the operation, the inflammation had worsened and had begun to suppurate, and three months after the operation, the element became detached from the skin.

EXAMPLE IX

Hydroxyapatite synthesized in the same manner as in Example VIII was mixed with $Ca_3(PO_4)_2$, $MgO$, $Na_2O$, $K_2O$, and $CaF_2$ in the same proportions as in Example II. A sinter in the form of a small column with an outer diameter of 3 mm containing a gold tube 1 mm in diameter was prepared from the resultant mixture in a manner similar to that described in Example III. The resultant sinter was abrasion treated with an abrasion to obtain a microtubular element having the shape shown in FIG. 5.

The sinter portion of the element had a length of 8 mm and an outer diameter of 2 mm.

A filter means for removing bacteria was then connected to the element, as shown in FIG. 6. This element was pierced and buried in the thorax of an adult dog so that the bottom thereof was located under the skin. About three weeks after the element was buried, the element was completely joined with the cutaneous tissue and implanted therein.

Next, the end of the element head was connected to a conduit filled with physiological saline to measure the DC resistance (an electrode for an electrocardiogram, Lectroad ®, manufactured by Advance Electrode Co., Ltd. was attached to another portion of the shaved thorax as a non-barrier member). As a result, a resistance value of 1.7 kΩ was obtained, confirming a remarkable reduction in resistance when compared with the usual cutaneous resistance through the keratin layer of approximately 100 kΩ.

EXAMPLE X

A synthetic resin cylinder equipped with a porous member (a Teflon resin film having an average pore diameter of 4μ) was provided in the transcutaneously implantable element prepared in Example VIII, as shown in FIG. 7, so as to provide a sample.

The sample was buried in the side abdominal skin of a crossbred adult dog and variations in the buried site over a period of time were observed. An excellent adaptability of the sample to the cutaneous tissue was found, as in Example IX.

EXAMPLE XI

A porous member made of an alumina sinter having an average pore size of 50μ was connected to the transcutaneously implantable element prepared in Example IX, as shown in FIG. 8. The resultant element was pierced and buried in the thorax of an adult dog so that the bottom thereof was located under the skin. Approximately three weeks after the element was buried, the element was completely joined with the cutaneous tissue and implanted therein.

The end of the element head was then connected to a conduit filled with physiological saline to measure the DC resistance (an electrode for an electrocardiogram, Lectroad ®, manufactured by Advance Electrode Co., Ltd. was attached to another portion of the shaved thorax as a non-barrier member). As a result, a resistance value of 3.8 kΩ was obtained, confirming a remarkable reduction in resistance when compared to the usual cutaneous resistance through the keratin layer of approximately 100 kΩ.

We claim:

1. A transcutaneously implantable element in which at least a portion thereof in contact with the cutaneous tissue of a living body is composed of a ceramic material comprising, as the main raw material, hydroxyapatite, and which comprises a through hole for mechanically connecting the interior and exterior of the living body to each other.

2. The element of claim 1 which is provided with a membrane filter for removing bacteria.

3. A transcutaneously implantable element for electrically or mechanically connecting the interior and exterior of a living body to each other in which at least a portion of said implantable element in contact with the cutaneous tissue of said living body is composed of a ceramic material comprising, as the main raw material, at least one member selected from the group consisting of hydroxyapatie, tricalcium phosphate and tetracalcium phosphate.

* * * * *

UNITED STATES PATENT AND TRADEMARK OFFICE
CERTIFICATE OF CORRECTION

PATENT NO. : 5,035,711
DATED : July 30, 1991
INVENTOR(S) : AOKI ET AL.

It is certified that error appears in the above-identified patent and that said Letters Patent is hereby corrected as shown below:

Title page, paragraph [63], line 5, the date of filing of Serial No. 110,539 should read October 20, 1987.

Column 1, line 11, the date of filing of U.S. Serial No. 110,539 should read October 20, 1987.

Col. 12, claim 3, line 8, the word "hydroxyapatie" should be --hydroxyapatite--.

Signed and Sealed this

Nineteenth Day of January, 1993

Attest:

DOUGLAS B. COMER

Attesting Officer

Acting Commissioner of Patents and Trademarks